(12) United States Patent
Wershing et al.

(10) Patent No.: US 10,842,406 B2
(45) Date of Patent: Nov. 24, 2020

(54) PORTABLE DEVICE FOR PROVIDING NON-CONTACT HEAT-EVOKED POTENTIALS

(71) Applicant: Forest Devices, Inc., Pittsburgh, PA (US)

(72) Inventors: Brycen L. Wershing, Pittsburgh, PA (US); Daniel C. Willis, Pittsburgh, PA (US)

(73) Assignee: Forest Devices, Inc., Pittsburgh, PA (US)

( * ) Notice: Subject to any disclaimer, the term of this patent is extended or adjusted under 35 U.S.C. 154(b) by 315 days.

(21) Appl. No.: 15/890,493

(22) Filed: Feb. 7, 2018

(65) Prior Publication Data

US 2018/0220919 A1     Aug. 9, 2018

Related U.S. Application Data

(60) Provisional application No. 62/456,304, filed on Feb. 8, 2017.

(51) Int. Cl.
*A61B 5/00* (2006.01)
*A61B 5/0484* (2006.01)

(52) U.S. Cl.
CPC .......... *A61B 5/0484* (2013.01); *A61B 5/4064* (2013.01); *A61B 5/4076* (2013.01); *A61B 5/6814* (2013.01); *A61B 5/6831* (2013.01); *A61B 2505/01* (2013.01)

(58) Field of Classification Search
CPC ... A61B 5/0484; A61B 5/4064; A61B 5/4076; A61B 5/6814; A61N 1/36014; A61N 1/36025; A61N 1/36082; A61N 5/0613
See application file for complete search history.

(56) References Cited

U.S. PATENT DOCUMENTS

| | | | |
|---|---|---|---|
| 4,930,317 A | 6/1990 | Klein | |
| 5,628,769 A * | 5/1997 | Saringer | A61F 7/007 607/98 |
| 6,017,302 A * | 1/2000 | Loos | A61B 5/00 600/28 |
| 6,052,619 A | 4/2000 | John | |
| 6,091,994 A | 7/2000 | Loos | |
| 6,381,488 B1 | 4/2002 | Dickey et al. | |

(Continued)

FOREIGN PATENT DOCUMENTS

| | | |
|---|---|---|
| DE | 10203049 B4 | 7/2004 |
| EP | 1648302 B1 | 1/2007 |

(Continued)

OTHER PUBLICATIONS

Atherton et al., "Use of the novel contact heat evoked potential stimulator (CHEPS) for the assessment of small fibre neuropathy: correlations with skin flare responses and intra-epidermal nerve fibre counts", BMC Neurology, 2007, vol. 7 pp. 21-30.

(Continued)

*Primary Examiner* — Max F Hindenburg

(74) *Attorney, Agent, or Firm* — The Webb Law Firm

(57) ABSTRACT

Provided herein is a device, a system, and a method of using the device and system to deliver non-contact thermal stimulation to the skin of a person and, by detecting evoked potentials in that person's central nervous system, to determine a neurological condition of the person.

20 Claims, 12 Drawing Sheets

(56) References Cited

U.S. PATENT DOCUMENTS

| | | |
|---|---|---|
| 6,840,955 B2 | 1/2005 | Ein |
| 7,024,238 B2 | 4/2006 | Bergethon |
| 7,087,075 B2 | 8/2006 | Briscoe et al. |
| 7,396,326 B2 | 7/2008 | Ghiron et al. |
| 7,471,978 B2 | 12/2008 | John et al. |
| 8,083,786 B2 | 12/2011 | Gafni et al. |
| 8,155,736 B2 | 4/2012 | Sullivan et al. |
| 8,236,038 B2 | 8/2012 | Nofzinger |
| 8,652,189 B2 | 2/2014 | Gafni et al. |
| 8,696,724 B2 | 4/2014 | Rogers |
| 9,204,807 B2 | 12/2015 | Leschinsky et al. |
| 9,283,111 B2 | 3/2016 | Rogers et al. |
| 9,398,931 B2 | 7/2016 | Wittenberger et al. |
| 9,681,980 B2 | 6/2017 | Swyer et al. |
| 2001/0049480 A1 | 12/2001 | John et al. |
| 2006/0224081 A1 | 10/2006 | Meyer et al. |
| 2007/0010860 A1* | 1/2007 | Gafni .................. A61B 5/0484 607/96 |
| 2012/0095535 A1 | 4/2012 | Gafni et al. |
| 2013/0018289 A1 | 1/2013 | Nussbaum et al. |
| 2013/0090546 A1* | 4/2013 | Stroman ................ A61B 5/055 600/411 |
| 2014/0197937 A1* | 7/2014 | Huang ................. A61H 9/0071 340/407.1 |
| 2014/0243941 A1 | 8/2014 | Rogers et al. |
| 2015/0127077 A1 | 5/2015 | Ben Asher et al. |
| 2015/0320592 A1 | 11/2015 | Black et al. |
| 2016/0238040 A1* | 8/2016 | Gallo .................... A61B 34/76 |
| 2016/0287127 A1 | 10/2016 | Kesinger et al. |
| 2017/0224526 A1 | 8/2017 | Dufour et al. |

FOREIGN PATENT DOCUMENTS

| | | |
|---|---|---|
| ES | 2316331 B2 | 10/2009 |
| KR | 101222317 B1 | 1/2013 |
| KR | 101453778 B1 | 10/2014 |

OTHER PUBLICATIONS

Chao et al., "Patterns of contact heat evoked potentials (CHEP) in neuropathy with skin denervation: Correlation of CHEP amplitude with intraepidermal nerve fiber density", Clinical Neurophysiology, 2008, pp. 653-661, Issue 119.

Chen et al., "Contact Heat Evoked Potentials in Normal Subjects", Acta Neurologica Taiwanica, 2006, vol. 15 Issue 3, pp. 184-191.

Hernandez, "Evoked Potentials as Neurophysiologic Tools to Evaluate Stroke", Journal of Neurology and Stroke, 2015, vol. 2 Issue 1.

Niedermeyer et al., "Somatosensory evoked potentials", Electroencephalography: Basic Principles, Clinical Applications, and Related Fields, 1999, 4th Edition, Williams and Wilkins, Philadelphia.

* cited by examiner

PORTABLE DEVICE FOR PROVIDING NON-CONTACT HEAT-EVOKED POTENTIALS

CROSS REFERENCE TO RELATED APPLICATION

This application claims the benefit of U.S. Provisional Patent Application No. 62/456,304, filed Feb. 8, 2017, the entire contents of which are hereby incorporated by reference.

BACKGROUND OF THE INVENTION

Field of the Invention

The present disclosure relates to systems, devices, and methods for generating heat-evoked potentials and monitoring the same. More particularly, the present disclosure relates to a device for applying heat to the skin of a person, detecting electrical potentials evoked thereby, and systems and methods for analyzing the evoked potentials to determine a physiological state of a person.

Description of Related Art

A cerebrovascular accident, or stroke, is a condition in which the flow of blood to one or more parts of the brain is interrupted. The loss of blood flow deprives the affected regions of the brain of oxygen and nutrients, resulting in cell death that can begin within minutes of the onset of the stroke. Because of the severe effects that a stroke can have on the brain, and on an individual's quality of life thereafter, early and rapid diagnosis of a stroke is of vital importance.

Despite the need for such rapid diagnosis, it can often be difficult to diagnose stroke-like symptoms accurately, without expensive, hospital-based equipment, which is generally not feasible for first responders to use in the field. Thus, an accurate diagnosis of a stroke is often dependent on the subjective assessment of the person's symptoms, or requires emergency personnel to bring individuals to the nearest hospital where the person may or may not receive adequate care. At present, only about 1 in 7 hospitals are currently configured as stroke centers.

Some systems possess the portability required to accurately diagnose a stroke in the field. U.S. Patent Application Publication No. 2016/0287127, incorporated herein by reference in its entirety, discloses a system of delivering electrical shocks to a person and detecting evoked potentials in the brain. However, the use of electrical shocks to evoke potentials include shortcomings.

The use of temperature changes to evoke potentials for analysis of neurological function is a promising alternative to electrical shock-evoked potentials. Contact heat evoked potentials (CHEPs) are a phenomenon that has previously been used to assess peripheral neuropathies (Chao et al. "Patterns of contact heat evoked potentials (CHEP) in neuropathy with skin denervation: correlation of CHEP amplitude with intraepidermal nerve fiber density." *Clin. Neurophysiol.* 2008; 119(3): 653-661). By measuring the brain's electrical response to spikes of increasing heat, brain deficiencies in some regions can be accurately determined. For example, a unilateral deficiency points to a stroke in the person's recent history. The neuroscience of these methods have been proven by CHEP devices, such as Peltier devices. However, the required associated devices, such as cooling devices for lowering skin temperature, are still too large, power consuming, and expensive to be used by first responders and others in a pre-hospital or emergency setting.

SUMMARY OF THE INVENTION

Provided in this disclosure is a thermal stimulation device that can be used by first responders and others to deliver thermal stimulation to a person for the purpose of producing evoked potentials that can be analyzed to determine the person's neurological state. In one aspect, the device includes a housing, an air circulator, a heating element, and an attachment mechanism to secure the device to a person.

Also provided in this disclosure are methods of producing evoked potentials based on thermal stimulation of a person's skin, including thermally stimulating a portion of the person's skin using the device described above, and detecting, with one or more sensors attached to the person, an evoked potential in the person's primary somatosensory cortex, somatosensory association cortex, and/or thalamus.

Also provided in this disclosure is a system including the thermal stimulation device described above, one or more sensors configured to be attached to the person, and a processor configured or programmed to analyze data from the one or more sensors to determine the person's neurological state.

Also provided in this disclosure is a method of determining a neurological condition in a person comprising thermally stimulating a portion of the person's skin with a device including a housing, an air circulator, a heating element, and an attachment mechanism to secure the housing to a person, detecting, with one or more sensors attached to the person, an evoked potential in the person's primary somatosensory cortex, somatosensory association cortex, and/or thalamus, receiving, with one or more processors, data relating to the evoked potentials, and analyzing, with one or more processors, the evoked potentials to determine a neurological condition of the person.

Further embodiments or aspects are set forth below.

In one non-limiting embodiment, provided is a portable thermal stimulation device for delivering thermal stimulation to a person for the purpose of producing evoked potentials, comprising: a housing; an air circulator configured to provide a current of air through the housing to a person's skin; a heating element configured to heat the current of air provided by the air circulator; and an attachment mechanism to secure the device to the person.

The portable thermal stimulation device may further comprise an insulating layer disposed at least partially within or on the housing.

The portable thermal stimulation device may have a housing that has a frustoconical shape.

The portable thermal stimulation device may have the air circulator positioned at least partially within the housing.

The portable thermal stimulation device may have the air circulator in the form of at least one of a pump, a compressor, a fan, a blower, and an impeller.

The portable thermal stimulation device may have the air circulator include a source of pressurized air.

The portable thermal stimulation device may further include one or more rechargeable batteries.

The portable thermal stimulation device may have the heating element positioned at least partially within the housing, optionally wherein the heating element is surrounded at least partially by an insulating layer.

The portable thermal stimulation device may have the heating element as at least one of an electrical heating element and a chemical heating element.

The portable thermal stimulation device may have the electrical heating element include a resistive element.

The portable thermal stimulation device may further include at least one temperature sensor disposed within the housing.

The portable thermal stimulation device, may further include a processor; and a non-transitory computer readable media storing programming instructions that, when executed by the processor cause the processor to analyze temperature data received from the one or more temperature sensors, compare the temperature data to a predetermined threshold, and adjust a temperature of the current of air based on the comparison.

The portable thermal stimulation device may include at least one temperature sensor configured to measure the temperature of the current of air within the housing and/or temperature of a portion of skin of the person to which the device is attached.

The portable thermal stimulation may further include at least one mechanism for controlling a temperature to which the current of air is heated.

The portable thermal stimulation device may further include one or more air-directing mechanisms configured to direct the current of air to one or more areas of the person's skin.

The portable thermal stimulation device may further include a source of air in fluid communication with the air circulator.

The portable thermal stimulation device may include the source of air as a cartridge attached to the housing.

The portable thermal stimulation device may further include at least two sources of air and one or more conduits for placing the at least two sources of air in fluid communication with the housing.

The portable thermal stimulation device may include at least one source of air as a source of cool air and at least one source of air as a source of warm air.

The portable thermal stimulation device may have the heating element operatively associated with the source of warm air.

The portable thermal stimulation device may include the one or more conduits as insulated.

The portable thermal stimulation device may further include a manifold or mixer in fluid communication with the at least two sources of air and the housing.

The portable thermal stimulation device may further include a cooling element adapted to cool the current of air provided by the air circulator.

In another non-limiting embodiment, provided is a method of producing evoked potentials in a person based on thermal stimulation of the person's skin, comprising: thermally stimulating a portion of the person's skin using the device described above; and detecting, with one or more sensors attached to the person, an evoked potential in the person's primary somatosensory cortex, somatosensory association cortex, and/or thalamus.

In the method, the person's skin may be thermally stimulated for from 1-1000 ms, optionally 100-500 ms, preferably 250 ms.

In another non-limiting embodiment, provided is a system for determining a neurological state of a person, comprising: the thermal stimulation device described above; one or more sensors configured to be attached to the person; a processor; and a non-transitory computer readable media storing programming instructions that, when executed, cause the processor to analyze data received from the one or more sensors and determine the person's neurological state.

In the system, the non-transitory computer readable media may store programming instructions that, when executed, cause the thermal stimulation device to thermally stimulate a portion of the person's skin.

A In another non-limiting embodiment, provided is a method of determining a neurological condition in a person, comprising: thermally stimulating a portion of the person's skin with the thermal stimulation device described above; detecting, with one or more sensors attached to the person, an evoked potential in the person's primary somatosensory cortex, somatosensory association cortex, and/or thalamus; receiving, with one or more processors and from the sensors, data relating to the evoked potentials; and analyzing, with one or more processors, the evoked potentials to determine a neurological condition of the person.

In the method, the person's skin may be thermally stimulated for from 1-1000 ms, optionally 100-500 ms, preferably 250 ms.

In the method, the person's skin may be stimulated 1-20 times.

DESCRIPTION OF THE INVENTION

Figure 1:
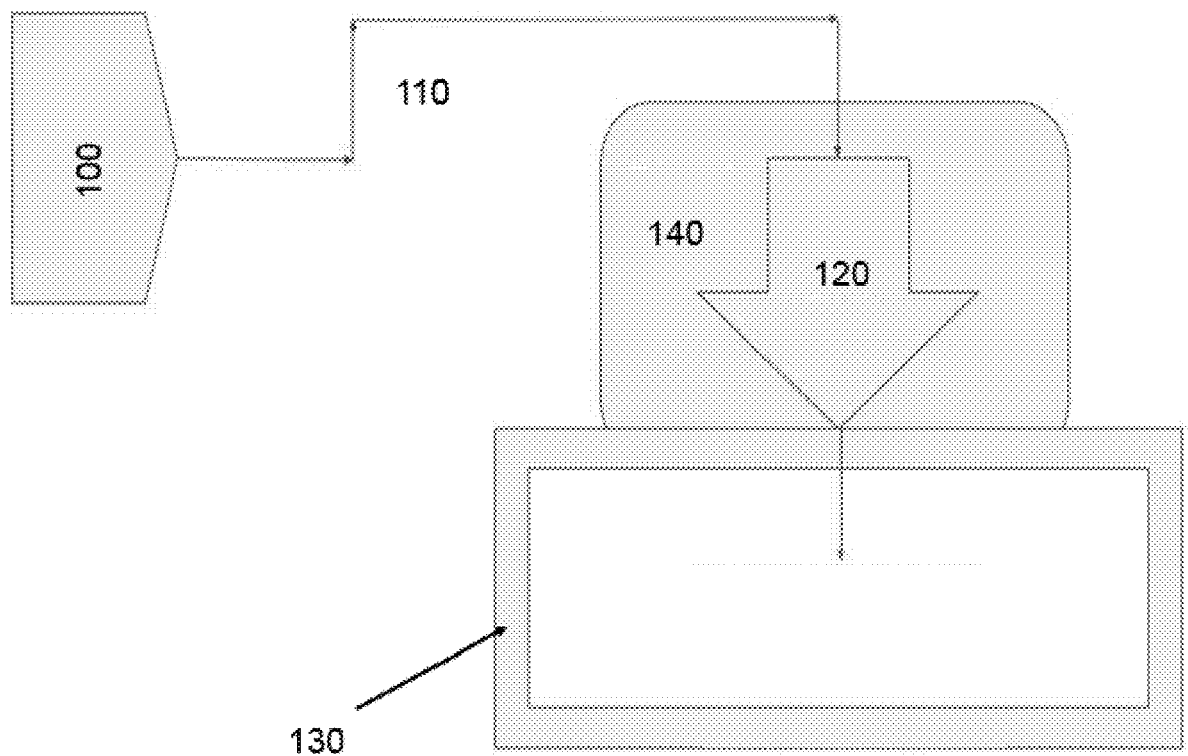
FIG. 1 shows a schematic illustration of a device according to one aspect of the present disclosure.

The following description is merely exemplary in nature and is in no way intended to limit the invention, its application, or uses. While the description is designed to permit one of ordinary skill in the art to make and use the invention, and specific examples are provided to that end, they should in no way be considered limiting. It will be apparent to one of ordinary skill in the art that various modifications to the following will fall within the scope of the appended claims. The present invention should not be considered limited to the presently disclosed aspects, whether provided in the examples or elsewhere herein.

The use of numerical values in the various ranges specified in this application, unless expressly indicated otherwise, are stated as approximations as though the minimum and maximum values within the stated ranges are both preceded by the word "about." In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

The figures accompanying this application are representative in nature, and should not be construed as implying any particular scale or directionality, unless otherwise indicated. For purposes of the description hereinafter, the terms "upper", "lower", "right", "left", "vertical", "horizontal", "top", "bottom", "lateral", "longitudinal" and derivatives thereof shall relate to the invention as it is oriented in the drawing figures. However, it is to be understood that the invention may assume various alternative variations and step sequences, except where expressly specified to the contrary. Hence, specific dimensions and other physical characteristics related to the embodiments disclosed herein are not to be considered as limiting.

As used herein, the terms "communication" and "communicate" refer to the receipt, transmission, or transfer of one or more signals, messages, commands, or other type of data. For one unit or device, to be in communication with another unit or device, means that the one unit or device is able to receive data from and/or transmit data to the other unit or device. A communication can use a direct or indirect connection, and can be wired and/or wireless in nature. Additionally, two units or devices can be in communication with each other even though the data transmitted can be modified, processed, routed, etc., between the first and second unit or device. For example, a first unit can be in communication with a second unit even though the first unit passively receives data and does not actively transmit data to the second unit. As another example, a first unit can be in communication with a second unit if an intermediary unit processes data from one unit and transmits processed data to the second unit. It will be appreciated that numerous other arrangements are possible. Any known electronic communication protocols and/or algorithms can be used such as, for example, TCP/IP (including HTTP and other protocols), WLAN (including 802.11 and other radio frequency-based protocols and methods), analog transmissions, Global System for Mobile Communications (GSM), BLUETOOTH, ZigBee, EnOcean, TransferJet, Wireless USB, and the like, known to those of skill in the art.

As used herein, the term "cool air" means air which is at, around, or below room temperature. For purposes of this disclosure, cool air is primarily air that will be heated by the heating element of the thermal stimulation device or will be used for cooling the heating element and/or a person's skin. Generally, for purposes of this disclosure, this will refer to air below about 110° F., such as below about 100° F.

As used herein, the term "warm air" means air which is at an appropriate temperature to generate a thermal stimulation when it comes into contact with a person's skin without causing injury or damage to the person's skin. Generally, for purposes of this disclosure, warm air is at a temperature of 113° to 140° F., such as 120° to 135° F.

As used herein, the term "hot air" means air which is too hot to be contacted with a person's skin, as it will cause too much pain or injury to the person. In this disclosure, hot air is typically cooled via mixing with cool air to create warm air which is then directed into contact with a person's skin. Generally, for purposes of this disclosure, hot air is air at a temperature above warm air, such as above 140° F.

As used herein, the term "evoked potential" means an increase in electrical activity elicited in the central nervous system of a person that results from a stimulus applied to that person.

As used herein, the terms "person," "patient," or "subject" refer to members of the animal kingdom including, but not limited to, human beings.

As used herein, the term "primary somatosensory cortex" means the postcentral gyrus, located in the anterior parietal lobe of the brain, the primary region of the brain receiving sensory impulses, including sensation of pain and temperature from the skin through the lateral spinothalamic tract.

As used herein, the term "lateral spinothalamic tract" means the sensory pathway that conveys information relating to pain and temperature from the skin via nociceptors and thermoreceptors to the ventral posterolateral nucleus of the thalamus.

As used herein, the term "thermoreceptor" means neurons activated by changes in temperature.

As used herein, the term "nociceptor" means neurons activated by damaging or potentially damaging (e.g., painful) stimuli caused by temperature difference from normal body temperature.

As used herein, the term "thalamus" means the forebrain subcortical structure responsible for relaying sensorimotor information to cortical areas including the primary somatosensory cortex.

As used herein, the term "ventral posterolateral nucleus of the thalamus" means the region of the thalamus in which resides cells that receive sensory input from neurons of the spinothalamic tract and which project to the primary somatosensory cortex.

As used herein, the term "somatosensory association cortex" means the posterior parietal cortex, or the region of the parietal lobe immediately posterior to the primary somatosensory cortex, which integrates information from the primary somatosensory cortex.

As used herein, the term "thermal stimulation" means stimulation of the skin using a change in temperature from ambient temperature, the change in temperature resulting in a stimulation of the person's skin that activates nociceptors.

As used herein, the term "somatotopic organization" means correspondence between distinct anatomical locations and distinct regions of primary somatosensory cortex that represent said anatomical locations. In other words, somatotopic organization means that stimulating the skin of a person's arm will reliably produce evoked potentials in a specific region of primary somatosensory cortex representative of the arm.

Described herein is a portable thermal stimulation device for delivering thermal stimulation to a person for the purpose of generating an evoked potential in the person. The evoked potential can then be analyzed to determine various neurological conditions associated with the person. The device can include a housing, an air circulator, and a heating element. The device can also include an attachment mechanism for securing the housing to a person. The housing can take on any shape, provided it is sufficiently sized, so as to be portable and capable of being carried in, for example, the back of an ambulance or police car or in an emergency kit that can be carried by a first responder or other individual. The housing can be made of any suitable material, including plastics and lightweight metals. In aspects, an insulating layer is included to thermally insulate the heating element (described below) from the housing, so as to prevent the housing from becoming overheated. The housing forms an internal cavity within which other elements of the device can be included, as described below.

The device also includes an air circulator for generating air flow in a certain direction. The air circulator can be a conventional and well known apparatus for generating air flow, such as a pump, fan, blower, impeller, and/or supply of pressurized air, such as, a pressurized air tank. The air circulator can be positioned at least partially, such as completely, within the housing of the device.

As would be appreciated by one of skill in the art, selection of the type of air circulator can affect the cost and ease of use of the device. For example, fans or blowers are economical and are able to move large quantities of air through small pressure differentials. However, these devices can use a large amount of electricity and occupy a significant amount of space. In contrast, pumps or compressors can be quite compact, and are able to move small amounts of air through large pressure differentials. However, these devices are expensive, heavy, and use a large amount of electricity.

Another possible air circulator is a pressurized air tank. Such tanks can come in many different shapes and sizes. For example, large tanks can be built into buildings and ambulances, while smaller tanks, such as pressurized air cartridges, can be configured such that they travel with the device or can even be built into the device itself. The air contained in these tanks can be normal atmospheric air. Alternatively, the contents of the tank could have a higher concentration of carbon dioxide or oxygen. Pressurized oxygen, for example, is generally already available in hospitals and emergency response vehicles. In addition, other gases, which could have some other advantage, such as, being more thermally dense and/or having a higher heat transfer coefficient, could be used. Thus, for purposes of this disclosure, "air" also includes "gas" unless otherwise indicated to the contrary. Appropriately sized tanks may, in many cases, have a smaller size, less weight, and lower cost than a pump, fan, or blower. Pressurized tanks also use no electricity, which can further reduce the complexity, weight, and cost of the device, particularly where the device is powered by a battery.

As discussed further below, the air circulator can work in conjunction with the heating element to deliver warm air to a person's skin so as to cause a thermal stimulation sufficient to activate the person's nociceptors. In addition, the air circulator can deliver cool air to the person, so as to rapidly cool the person's skin after the thermal stimulation occurs. The air circulator can also deliver cool air to the heating element to quickly return the heating element to ambient temperature. Unlike Peltier devices currently known in the art, this rapid cooling of the skin is achievable with the device disclosed herein through the use of the air circulator, since there is not direct contact between the heating element and the person's skin. The air circulator, no matter which type is used, should be capable of cooling the skin from the thermal stimulation temperature to ambient temperature within a short period of time, such as three seconds or less or one second or less.

The device also includes a heating element. The heating element can be any apparatus capable of generating a sufficient amount of heat to heat air to an appropriate temperature. For example, in certain aspects, heating can be achieved electrically and/or chemically. With regards to electric heating, electric devices can include a resistive element which provides heat to its surroundings when current is passed through the resistor, such as a heating coil. Use of a heating coil is advantageous since it is a particularly energy-efficient process in terms of the amount of electricity required. In some embodiments, depending on the energy available to operate the device, selection of a more energy efficient heating element (such as a heating coil) can allow for a less energy efficient air circulator (such as a pump or fan), and vice versa.

With regard to chemical heating, the heating element can be in the form of a solution of liquid(s) contained within a thermally conductive casing where heat, generated by the liquids transfers through the conductive casing and comes into contact with the surrounding air. Alternatively, a chemical can be applied to a person's skin which is then activated to generate heat when air from the device is brought into contact with the chemical.

The particular arrangement of the elements of the device in relation to one another can take on various forms. For example, with regard to the placement of the heating element, there are various possibilities that will function for providing a stimulus sufficient to evoke a potential. In one non-limiting embodiment, when a pressurized tank or other contained source of air is used either as, or in combination with, the air circulator, the heating element can be submerged in the stored air so as to maintain the air at a specified temperature. This embodiment provides for near-instantaneous access to heated air without the need to first bring a heating element up to the desired temperature.

In another non-limiting embodiment, the heating element can be in-line with the air circulator so that the air circulator passes the air through and/or around the heating element in order to heat the air. The advantages of this in-line arrangement include electrical efficiency as the heating element need only be heated on a periodic basis. In addition, air can more readily be delivered at different temperatures in this embodiment by varying the heat generated by the heating element, such as by varying the current supplied to a resistive heating element.

In certain aspects, the heating element, whether electrical or chemical, is thermally separated from the housing by an insulating layer to protect the housing, person, and device operator. Materials, suitable for forming the insulating layer, are those that conduct heat poorly and are known to those of skill in the art. These include, without limitation, silicone-based polymers, natural and synthetic rubbers, heat-resistant plastics, and polystyrene foams.

In certain embodiments, the device can also include, either as part of the housing or as a separate component, one or more conduits to direct air between the air circulator, the heating element, and the person's skin. For example, in embodiments in which the air circulator is a pressurized tank and the heating element is submerged/immersed in the air source, a conduit can be used to direct air from the air source to the person's skin. By way of another example, in embodiments where the heating element is in-line with the air circulator, a first conduit can serve as a passage between the air circulator and the heating element, and a second conduit can serve as a passage between the heating element and the person's skin. In some embodiments, the first and second conduits may be separate sections of the same continuous conduit, such as a tubular member, which has the air circulator disposed near one end and a heating element disposed between the air circulator and the second end.

In certain embodiments, the conduits can be part of the housing and formed from the same materials as the housing. The conduits can also be formed from an insulating material or, alternatively, could have a layer of an insulating material attached to the interior surface thereof. Use of an insulating material can ensure that little to no variation of the air temperature occurs as the air travels through the conduit. As would be appreciated by one of skill in the art upon reading this disclosure, the location of the conduit may dictate the material of its construction since those conduits through which warm or hot air is intended to travel are more likely to benefit from an insulating material. Insulating materials are known to those of skill in the art, and include, without limitation, silicone-based polymers, natural and synthetic rubbers, heat-resistant plastics, and polystyrene foams. One end of the conduit can also include a tapered section which creates an air directing tip which focuses the air flow into a smaller area. The air directing tip can be provided at the end of the conduit which is intended to be placed against or near to the person's skin when using the device.

The device described herein can be controlled in a variety of ways including through a control system having internal control elements, external control elements, and/or manual control elements. The control system can also rely upon some measure of feedback. Feedback can be implemented in a variety of ways. In certain non-limiting embodiments, feedback is provided through temperature-based feedback and/or response-based feedback. Use of temperature-based feedback allows the device to adjust, for example, the temperature of the heating element based on either a measured output temperature of the air leaving the device or measured skin temperature of the person's skin at or near the location, where the air from the device comes into contact with the skin. In either aspect, the device further includes one or more temperature sensors to measure the output temperature and/or skin temperature. Response-based feedback allows the device to modulate output temperature based on the reaction of the individual to the stimulus. Such response-based feedback is most useful in an external control scheme, which is described below. In some embodiments, the device includes both temperature-based feedback and response-based feedback.

With regard to the control system, the device can include internal control elements, such as, a controller that is part of the device and stored within the housing. The device can further include a processor and non-transitory memory for storing programming instructions which, when executed by the processor, cause the processor to control the functioning of the device, including by adjusting the air flow produced by the air circulator and the output temperature as determined, at least in part, by the temperature of the heating element. This control can be based on timing and/or feedback (temperature-based or response-based, as described above).

An external control element can be in the form of a remote control device that works with the internal processor to control airflow and output temperature based on timing and/or feedback. The external control element can be any suitable device that can communicate with the internal control element of the device such as, for example, a personal digital assistant, a tablet, a smart watch, a portable computing device, a laptop, a palmtop, a mobile device, a mobile telephone, a server, or any other type of computing device. Such communication can be a wired, direct connection between the external controller and the device through, for example, and without limitation, a universal serial bus (USB) connection, or wireless, through a known wireless communication protocol such as TCP/IP (including HTTP and other protocols), WLAN (including 802.11 a/b/g/n and other radio frequency-based protocols and methods), analog transmissions, Global System for Mobile Communications (GSM), BLUETOOTH, ZigBee, EnOcean, TransferJet, Wireless USB, and the like, known to those of skill in the art. The processor and non-transitory memory for storing programming instructions discussed above can be located in the external control element. In some aspects, the external control element is part of a larger system that detects and analyzes the evoked potentials, as described below.

A manual control element can provide the operator the ability to control temperature and/or timing through a user interface. The user interface can be as simple as analog controls for temperature and an actuator, such as a button, for delivering the stimulus to the person's skin. In other aspects, the user interface can be a graphical user interface and an input device, for example, a touchscreen. The manual control element can be located on the device or on an external control element, such as a remote control. Those of skill in the art will appreciate that the type of user control is not limiting, so long as it allows a user to control temperature and delivery of the stimulus.

The device can also include an attachment mechanism to secure the device to a person's body, including the person's skin surface. By securing the device to a person's body, a rescuer or first responder can operate the device and tend to other activities without having to devote attention to physically maintaining contact between the device and the person's skin. Suitable attachment mechanisms include straps, belts, and the like, formed from elastic or resilient materials, allowing the device to be secured by the resilient nature of the material. In other aspects, the attachment mechanism can include non-elastic materials with fasteners, such as hook-and-loop (VELCRO) attachments, buckles, snaps, ties, and the like. In still other aspects, the attachment mechanism can be in the form of an adhesive material disposed on the exterior of the housing to secure the device to the person. For example, the adhesive may be disposed at the portion of the device that is to be placed against the skin surface (such as an end of a conduit) so as to maintain that portion of the device in the correct location. Combinations of the above attachments mechanisms (e.g., an adhesive and a strap disposed at different portions of the device) can also be used. Those of skill in the art will understand that the type of material and fastener can vary, so long as the attachment mechanism does not impair the ability of the device to achieve rapid thermal stimulation and return to ambient temperature of the person's skin.

While the device, as described herein, utilizes far less energy than Peltier devices and their associated cooling devices, the device does require energy to function. Suitable sources of energy can include batteries, rechargeable or otherwise, DC current from a vehicular source, and/or AC current from a traditional outlet (or a vehicular outlet that has been inverted). If one or more batteries are used, the battery can be included in the housing and can be removable, or can be rechargeable and permanently sealed in the housing. Those of skill in the art will appreciate that the source of power can vary, so long as the device is capable of delivering heated air to a person's skin on demand and with accuracy.

The components of the device described herein, including the air circulator, heating element, attachment mechanism for connecting the device to the body, and, in some aspects, the conduit(s), can be arranged in a number of ways to provide a low-cost, efficient device for delivering thermal stimulation. With reference to FIG. 1, shown is an arrangement of components according to one aspect of the present invention, including an air circulator/supply (100) which forces cool air (110) through an in-line heating element (120), which is attached to a person's body via an attachment mechanism (130). The heating element is in a fixed position within a thermal layer (140) and can operate by rapidly heating up and cooling down, thus providing a way to vary the temperature of the air delivered to a person. Delivery of cool air across the heating element can assist the cool down of the heating element.

Figure 2:
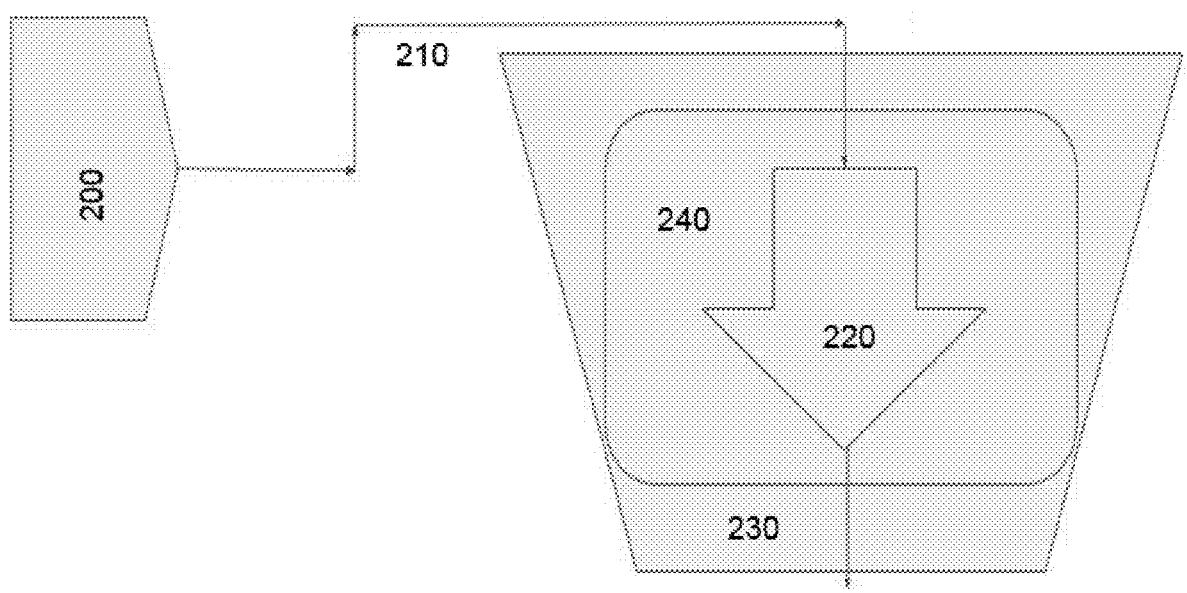
FIG. 2 shows a schematic illustration of a device according to another aspect of the present disclosure.

With reference to FIG. 2, shown is an arrangement of components according to another aspect of the present invention, including an air circulator/supply (200), which forces cool air (210) through the in-line heating element (220) that is contained within a handheld encasement (230). In non-limiting embodiments, the handheld encasement (230) includes a thermal layer (240) that at least partially surrounds the heating element (220). The heating element (220) varies how much heat is output, and thus, can change the temperature of the air delivered. In another aspect consistent with FIG. 2, the heating element (220) provides a constant output temperature, and the user can then vary the heat provided to the person by, for example, moving the device toward and away from the person's skin.

Figure 3:
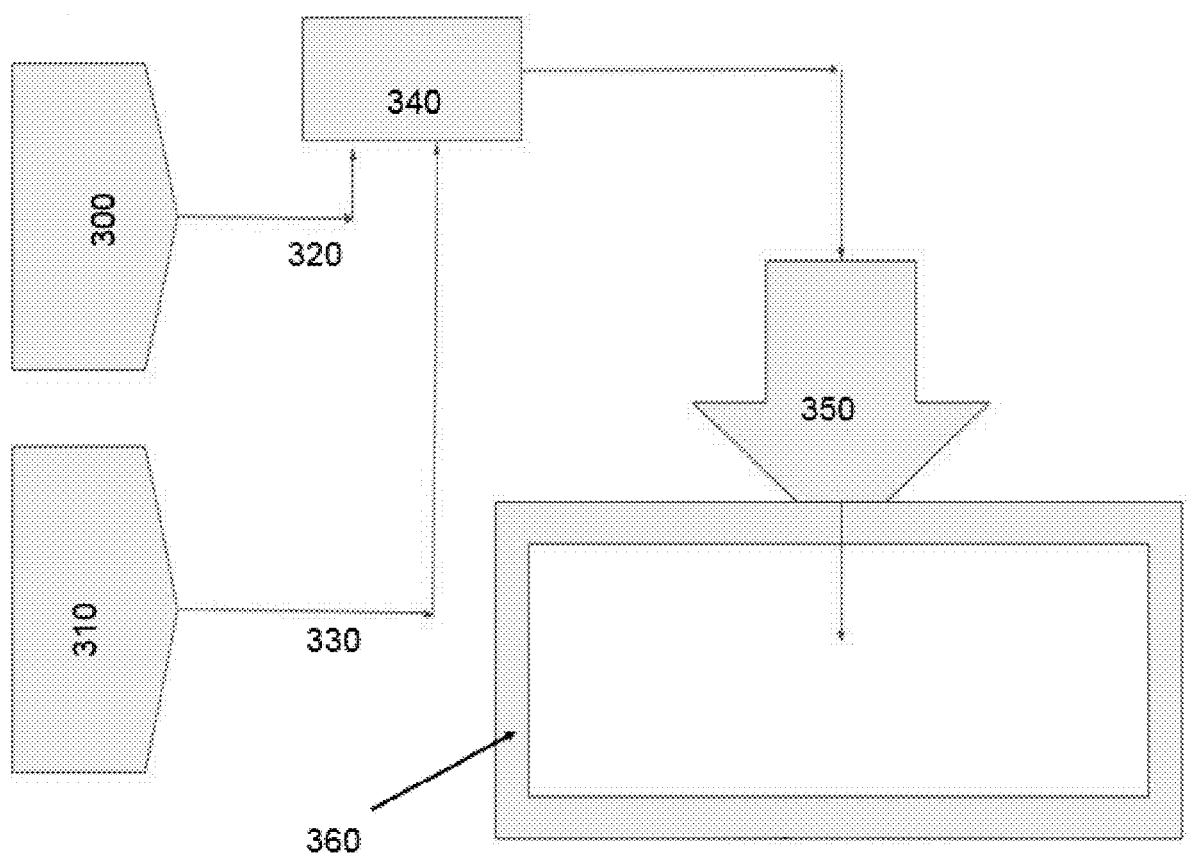
FIG. 3 shows a schematic illustration of a device according to another aspect of the present disclosure.

With reference to FIG. 3, shown is an arrangement of components according to another aspect of the present invention, including both a cool air circulator/supply (300) and a warm air circulator/supply (310). These air sources provide cool air (320) and warm air (330) to either a two-state or three-state manifold (340). With a two-state manifold, the two states would be cool air and warm air output. With a three-state manifold, the three states would be cool air, warm air, and no output. A valve within the manifold, and controlled by the control system, can determine which of the inputs passes through the manifold and toward the air directing tip (350), which is positioned near the person's skin by way of an attachment mechanism (360). In this embodiment, the heating element can be immersed in the warm air supply, as discussed above, or can be provided in-line upstream of the manifold(s).

Figure 4:
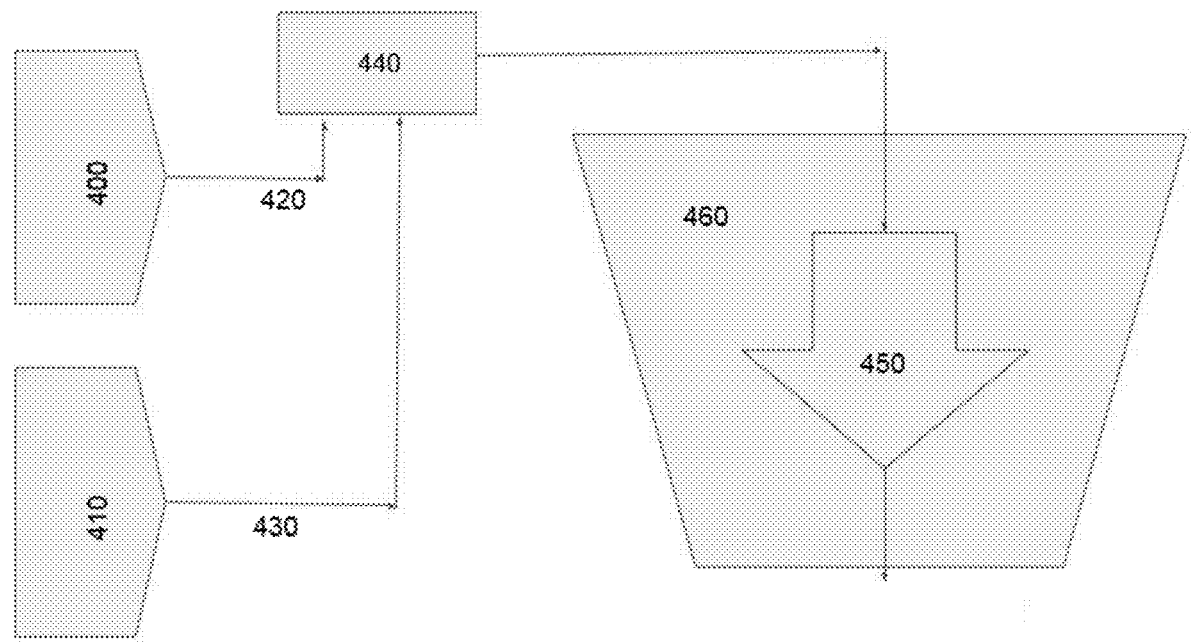
FIG. 4 shows a schematic illustration of a device according to another aspect of the present disclosure.

With reference to FIG. 4, shown is an arrangement of components according to another aspect of the present invention, including both a cool air supply (400) and a warm air supply (410) similar to FIG. 3. These air sources are used as the inputs of cool air (420) and warm air (430) to either a two-state or three-state manifold (440), as described above. This air would be directed to an air directing tip (450) which is encased in a handheld encasement (460). In this aspect, the housing would be held by the provider, though it could also be attached to the person's body.

Figure 5:
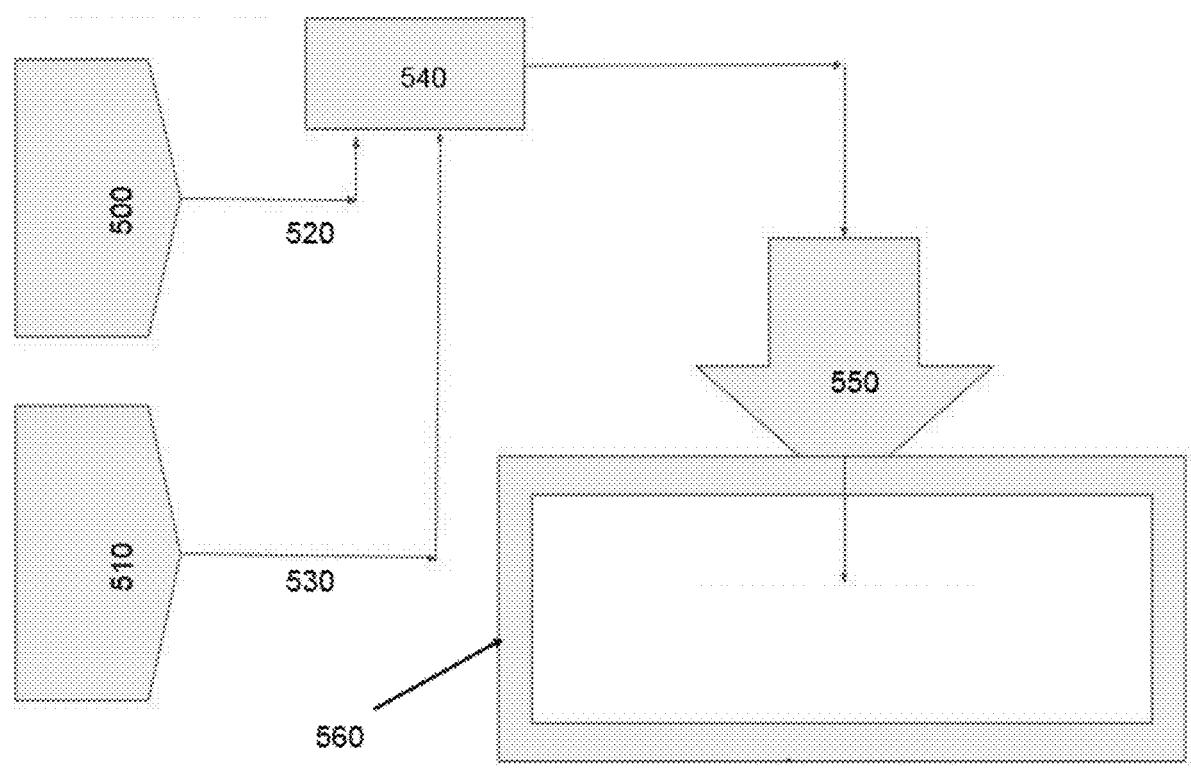
FIG. 5 shows a schematic illustration of a device according to another aspect of the present disclosure.

With reference to FIG. 5, shown is an arrangement of components according to another aspect of the present invention, including both a cool air supply (500) and a hot air supply (510). These air supplies are used as supplies of cool air (520) and warm air (530) the inputs to a mixer (540). The amount of each air supply that is input to the mixer can be controlled by a control system by operating valves associated with each air supply. This mixer, also controlled by the control system, would control the temperature and amount of air which would be provided to an air-directing tip (550) by allowing the cool air and hot air to mix. A valve could be used to control the output of the mixer. The air-directing tip (550) is attached to the person's body by an attachment mechanism (560). In this embodiment, the heating element (not shown) can be submerged in the hot air supply or provided in-line upstream of the mixer.

Figure 6:
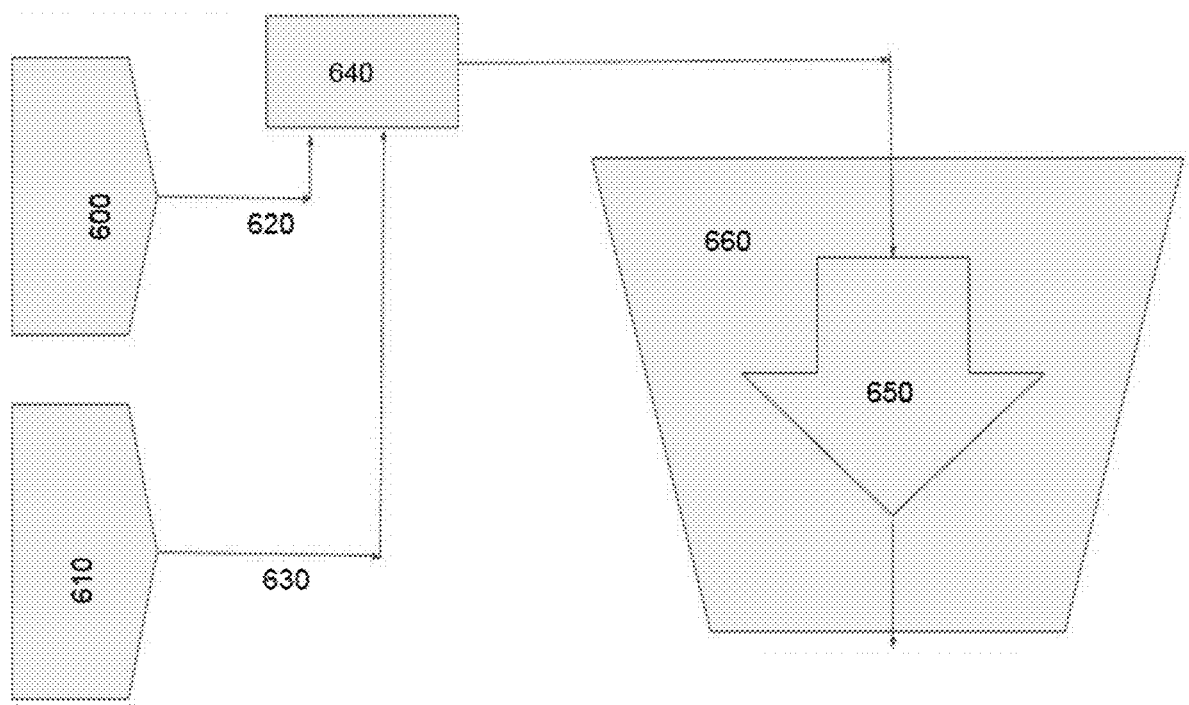
FIG. 6 shows a schematic illustration of a device according to another aspect of the present disclosure.

With reference to FIG. 6, shown is an arrangement of components according to another aspect of the present invention, including both a cool air supply (600) and a hot air supply (610) similar to FIG. 5. These sources of air are used as inputs of cool air (620) and hot air (630) to a mixer (640). The mixer controls (640) the temperature and amount of air that is provided to the air-directing tip (650). The tip in this aspect is encased in a housing (660), which is held by the provider or attached to the person's body via an attachment mechanism (not shown).

Figure 7:
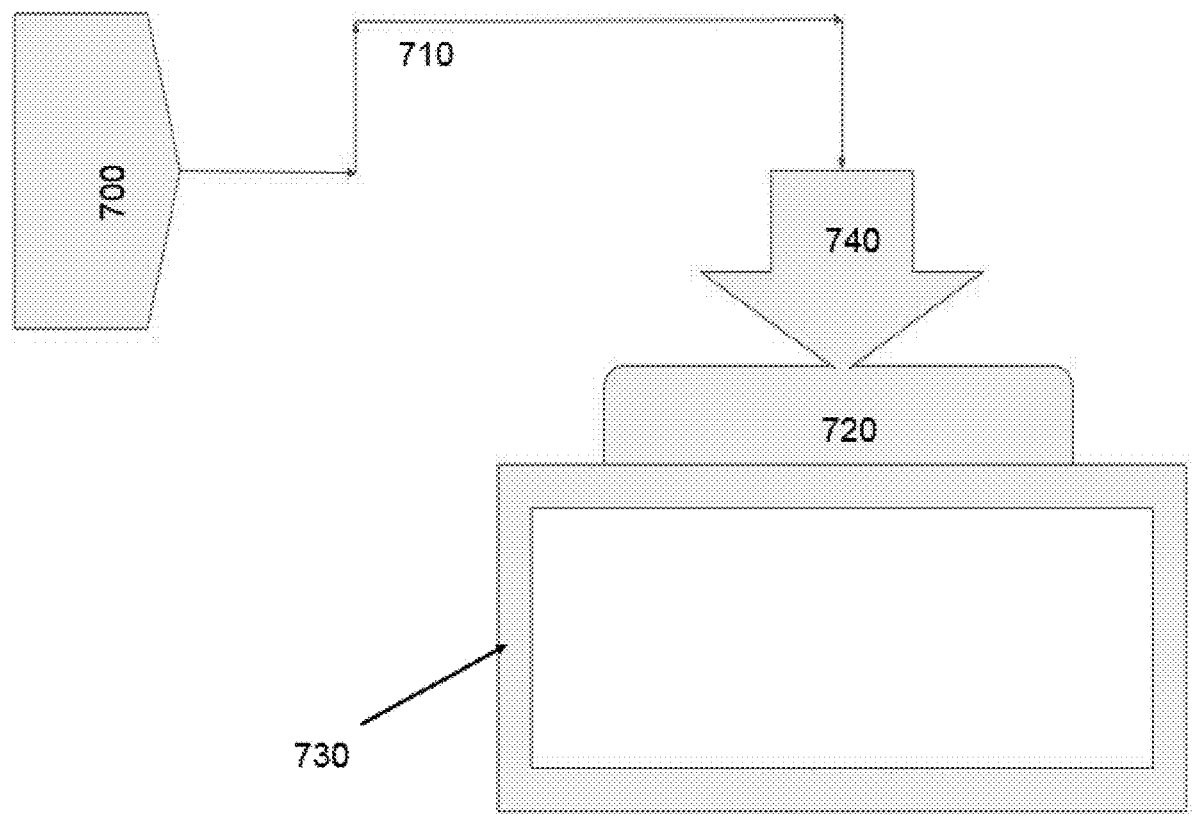
FIG. 7 shows a schematic illustration of a device according to another aspect of the present disclosure.

With reference to FIG. 7, shown is an arrangement of components according to another aspect of the present invention, including a cool air supply (700), which directs air to a heating element (720). The heating element is directly attached to the person's skin (by attachment mechanism (730)), and the heating element (720) will heat up and deliver heat by conduction before being cooled by the cooling device (740), which utilizes the cool air.

Figure 8:
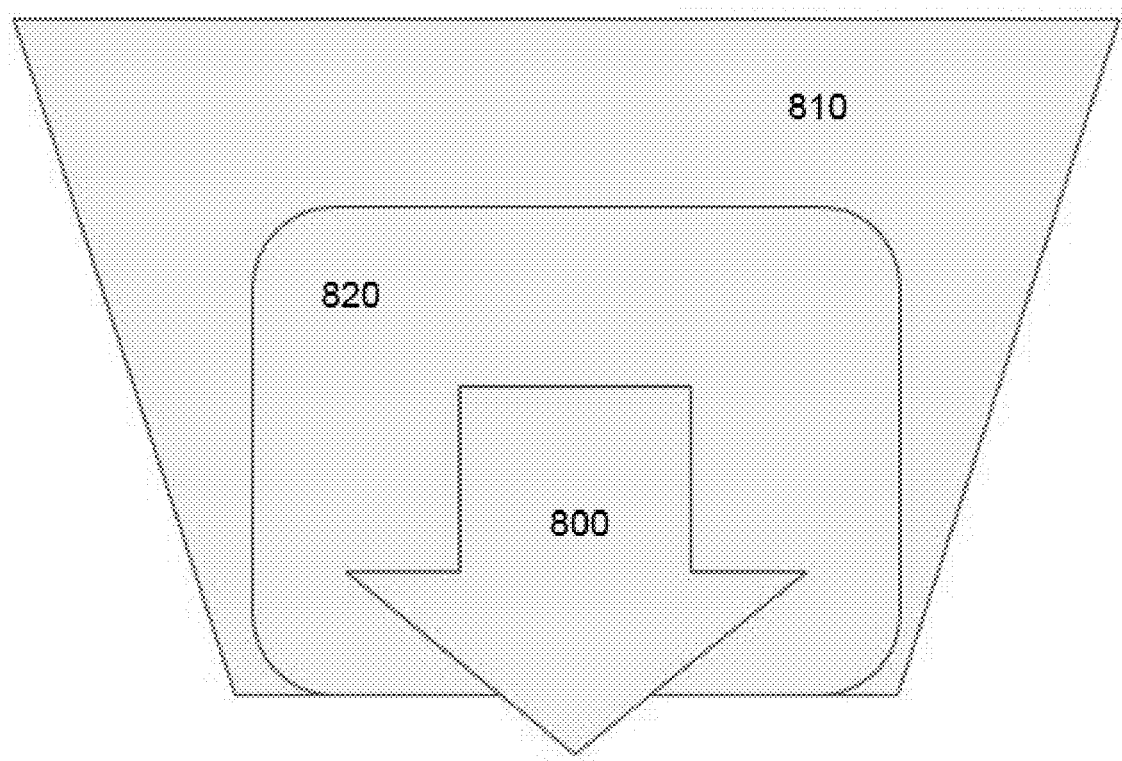
FIG. 8 shows a schematic illustration of a device according to another aspect of the present disclosure.

With reference to FIG. 8, shown is an arrangement of components according to another aspect of the present invention, including a heating element (800), which is encased in the housing (810) via a thermal layer (820). This heating element (800) outputs a constant temperature, and the provider would quickly touch the person with the heating element. The device can include a proximity sensor (not shown), such as one that detects when the provider touches the person with the device, or another structure for providing feedback, such as temperature of the heating element (800) or a feedback based on neurological response. This would be a very short touch, taking about half a second or less.

Figure 9:
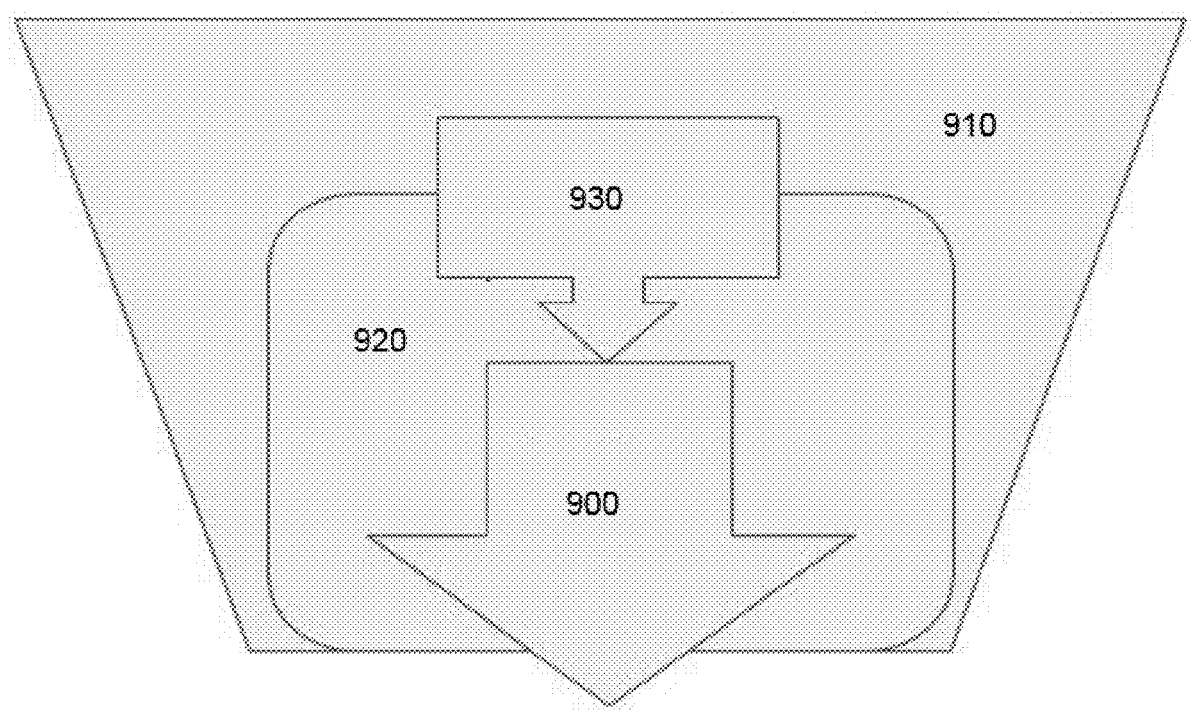
FIG. 9 shows a schematic illustration of a device according to another aspect of the present disclosure.

With reference to FIG. 9, shown is an arrangement of components according to another aspect of the present invention, including a heating element (900), which is encased in the housing (910) via a thermal layer (920). This heating element outputs a constant temperature, and the provider would hold the device against the person's skin. A mechanical actuator (930), within the housing, then moves the heating element in contact with the person's skin and then removed from contact with the person's skin to deliver the stimulus.

Figure 10B:
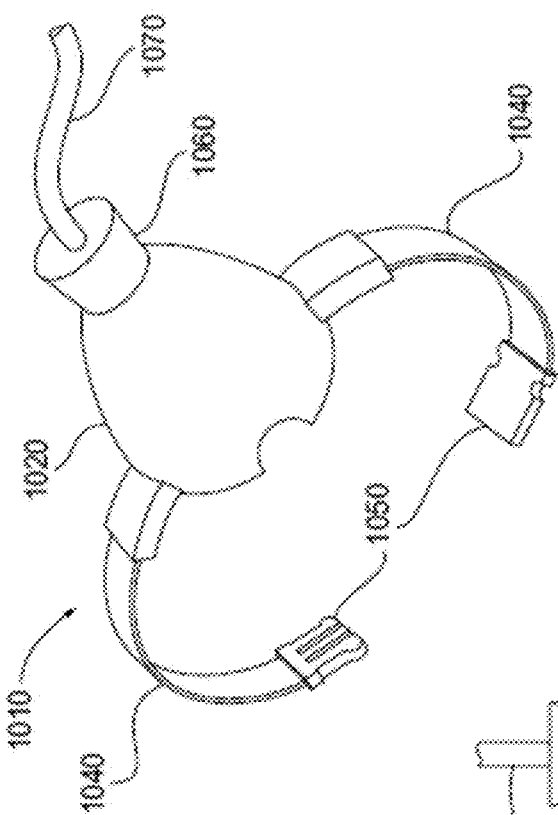
FIGS. 10A-10D show (A) top, (B) perspective, (C) front, and (D) side views of a device according to an aspect of the present disclosure.
Figure 10A:
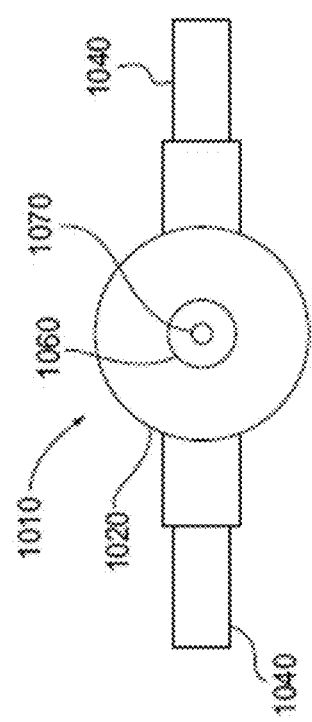
Figure 10D:
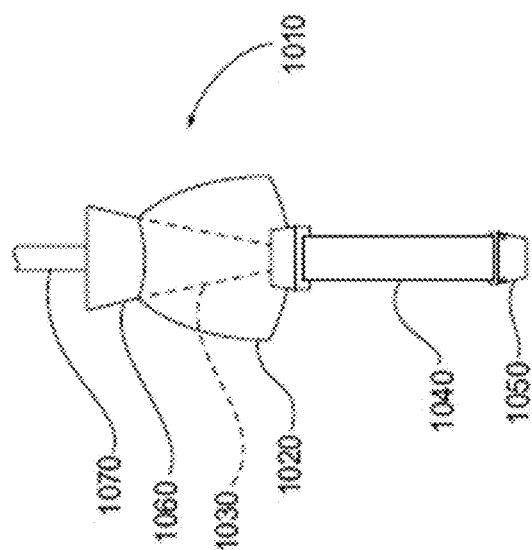
Figure 10C:
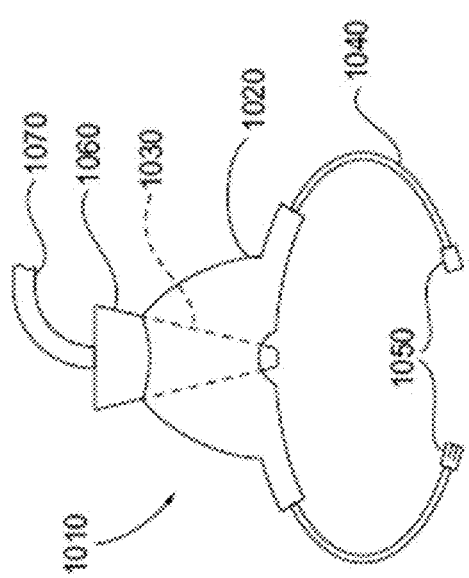

With reference to FIGS. 10A-10D, shown are various views of a device according to an aspect of the present invention. FIG. 10A is a top view, FIG. 10B is a perspective view, FIG. 10C is a front view, and FIG. 10D is a side view. Device (1010) includes housing (1020) containing a heating element (1030). The heating element may be any heating element described herein, so long as it can heat air sufficiently to evoke a potential. Device (1010) is removably attachable to a patient through a strap (1040) and buckle (1050), though, as described herein, the attachment may be by any suitable means to allow thermal stimulation to be delivered to a patient's skin. Device (1010), in the illustrated aspect, includes thermal insulation (1060), so that heated air maintains sufficient temperature to produce a heat-evoked potential and to allow a user to contact the housing without experiencing a burn or other unwanted injury. Air enters the housing through input (1070) from an air circulator or other source of air as described herein. In the illustrated aspect, the air is heated by heating element (1030) and directed to a patient's skin to deliver thermal stimulation and evoke a central potential to be measured by appropriate sensors. While not shown, a temperature sensor can be included for receiving feedback and controlling the temperature of the delivered air.

In use, the device can be used to evoke potentials by delivering thermal stimulation to the skin of a person, and these potentials can then be analyzed to identify or explore a variety of neurologic disorders including, without limitation, peripheral small nerve disease (including C and A-delta fiber disease), whether of idiopathic origin or as a result of diabetes, multiple sclerosis, or chemotherapy treatment, neuropathies, and strokes (including transient ischemic attacks (TIAs)). The thermal stimulation provided by the device can also be useful in the diagnosis of peripheral neuropathy. Specifically, the nature of pain response in the brain causes electrical potential spikes which are significantly above the noise floor. One can use an electroencephalogram (EEG) to bilaterally detect wavelets, which would occur about 100 ms to 2000 ms after the thermal stimulation is delivered. In a healthy, neurologically intact person, these wavelets are equal bilaterally in both magnitude and timing. An unexpected delay or magnitude can be indicative of neurological dysfunction, while bilateral asymmetry can be an indicator of a recent stroke. In certain aspects, the person is one who is, or is believed to be, experiencing stroke-like symptoms, or is one who has, or is believed to have, suffered a stroke.

The device can be configured or positioned in any manner suitable to stimulate thermoreceptors and/or nociceptors by thermally stimulating the skin on an accessible portion of the person's body, thus evoking one or more action potentials in the person's primary somatosensory cortex, somatosensory association cortex, and/or the thalamus. More specifically, stimulating thermoreceptors and/or nociceptors activates the spinothalamic tract, stimulating neurons in the ventral posterolateral nucleus of the thalamus, which causes action potentials in somatotopically-representative areas of primary somatosensory cortex.

The device can be used to deliver thermal stimulation to any part of the body and, thereby, elicit an evoked potential. For example, if the device is used within a system (such as the system described below) that includes one or more sensors attached to a person's head and neck to monitor the evoked potentials, the location on the person's head and neck, to which the sensors are attached, can correspond to the location of thermal stimulation, based on the somatotopic organization of the primary somatosensory cortex. In another embodiment, the thermal stimulation is delivered to the person's arm. After delivering the thermal stimulation, the device can quickly cool the person's skin by deactivating the heating element (if an in-line heating element is used) and delivering cool air to the person's skin using the air circulator. Once the person's skin has been sufficiently cooled, the process of generating the thermal stimulation can be repeated.

In certain aspects, the device is used to deliver thermal stimulation to the person's skin for from 1-1000 ms, all ranges inclusive. In a preferred aspect, the device delivers thermal stimulation to the person's skin for approximately 100-500 ms, ±50 ms. In a most preferred aspect, the device delivers thermal stimulation to the person's skin for 250 ms, ±50 ms. The device can, through provision of air heated to a temperature range of from 100-200° F., all ranges inclusive, heat a patient's skin to activate nociceptors. In other aspects, the device can provide cold air to activate nociceptors and stimulate an evoked potential.

In certain embodiments, in order to acquire more information about the person's neurological status, the device described herein can be used in combination with an apparatus for stimulating somatosensory evoked potentials (SSEPs). The combination of thermal stimulation and SSEPs can be accomplished using two separate and distinct devices, or the necessary components, to achieve the two functions, can be combined into a single device. In either aspect, the control systems described herein could control both functions. For example, in aspects where the two functions are performed by the same device, SSEP pads can be attached to the device to allow easy connection to the person. Devices and methods for delivery of stimuli to produce SSEPs are known to those of skill in the art and are described in, for example, Mauguiere (1999). E. Niedermeyer & F. Lopes da Silva, ed. "Somatosensory evoked potentials". Electroencephalography: basic principles, clinical applications and related fields. Williams and Wilkins, which is incorporated herein by reference.

The device described above can be used to detect asymmetry in pain threshold/responses. Such asymmetries can be utilized to provide an indication of a neurologic condition. Methods for determining a difference in pain threshold can make use of only the device described above, and do not require sensors for detecting evoked potentials or a computing device/system for data collection and analysis, as will be described below. However, in aspects, the device can be used with one or more sensors and/or computer systems to determine pain thresholds and asymmetries therein in a patient.

Also disclosed is a system, including the device described above, one or more sensor electrodes for detecting an evoked potential, and a computing device. An exemplary system with which the above-described device can function to determine a neurological condition in a person is described in U.S. Patent Application Publication No. 2016/0287127, incorporated herein by reference in its entirety.

In such a system, the one or more sensors for detecting evoked potentials are attached to the person and are in communication with the computing device, such that electrical potential data from the person is transmitted to the computing device for processing. This communication may be wired, with typical wired sensor electrodes available commercially, or the communication may be wireless, through any known wireless communication protocol. Any number of sensors can be used, and the sensors are typically placed at a location on the person's head or neck to provide adequate coverage and accurate analysis of evoked potentials. Suitable numbers of and locations for the sensors are provided in U.S. Patent Application Publication No. 2016/0287127, incorporated herein by reference in its entirety.

While a typical arrangement of sensors adheres to the international 10-20 system commonly associated with electroencephalography, as few as two sensors (optionally including a ground or reference sensor) can be used to adequately determine the presence/amplitude of evoked potentials. In one embodiment, at least one sensor is positioned above the parietal lobe of the person's brain and is configured to detect evoked potentials from the postcentral gyrus. Suitable electrodes include pad electrodes that can be attached by adhesive(s) or other suitable means, or single electrodes/an array of electrodes provided individually or in a grouping, such as in a cap, band, strap, or the like, that can be attached to the person's head for detecting potentials evoked by the thermal stimulation.

In certain aspects, a conductive gel or paste, for example and without limitation Ten20 Conductive Paste (Weaver and Company, Aurora, Colo.), can be included or pre-packaged with/pre-applied to the sensors, or can be applied by the first responder or rescuer when the sensors are attached to the person. In some aspects, the person's skin can be prepped with alcohol and/or an abrasive, for example, and without limitation Nuprep (Weaver and Company, Aurora, Colo.) prior to attaching the sensors to lower impedance between the skin and the sensors.

The computing device includes the appropriate processing mechanisms and computer-readable media for storing and executing instructions, such as programming instructions. The computing device includes a processing unit (typically referred to as a central processing unit, processor, or controller) that serves to execute instructions received in the appropriate data form and format. In the present system, the processor can receive instructions from an input device into which a user may enter commands, information, and data such as a keyboard, a mouse, etc., via a user input interface. The processor/processing unit may be in the form of multiple processors executing code in series, in parallel, or in any other manner for appropriate implementation of the computing device-based instructions. The computing device may operate in a network environment through the use of a communications device, which is integral to the computing device or remote therefrom.

The computing device can be in communication with, for control of, the thermal stimulation device described herein, and can also be in communication with one or more sensors for receipt of data relating to the evoked potentials. Such a system may be referred to as a neurological condition detection system. In certain aspects where the system is used by first responders or rescuers for detecting a neurological deficit associated with, for example, a stroke, and providing an initial diagnosis thereof, the system can be referred to as a stroke detection system. The computing device can, with user input or independently thereof based on programmed software, deliver thermal stimulation at various, random, or pre-determined timepoints, as will be described more thoroughly below, and through analysis of the presence and/or amplitude of evoked potentials compared to expected thresholds, determine whether or not a stroke is occurring/has occurred.

The stroke detection system can be positioned in an ambulance, such as a truck, van, bus, helicopter, boat, airplane, or other type of vehicle used by medics to transport persons. In some embodiments, it is contemplated that the computing device can also be configured to communicate the data collected from a person to a computer system of the hospital to which the person is transported so that the collected data can be used by medical staff of that hospital when treating the person. For instance, the computing device may be configured to transmit the collected data to a hospital communication device.

Also provided herein are methods of determining the neurological condition of a person based on the detection and analysis of evoked potentials that result from thermal stimulation using the system as described above. Specifically, in an aspect, the method includes the steps of thermally stimulating a person's skin with a device as described above, detecting, with one or more sensors attached to the person, an evoked potential in the person's primary somatosensory cortex, somatosensory association cortex, and/or thalamus, receiving, with one or more processors, data relating to the evoked potentials, and analyzing, with one or more processors, the evoked potentials to determine a neurological condition of the person. As described above, the thermal stimulation can be delivered to any appropriate area of the person's skin, with the proviso that the sensors are arranged on the person's head in a somatotopically-appropriate manner.

As described above, the evoked potentials of the person's brain are sensed by the one or more sensors attached to the person's head, effectively similar to an EEG, which sensors communicate data to the computing device to determine whether there is an asymmetric pathology. For example, if there is determined to be an asymmetric pathology, such that one side of the person's brain has a substantially different nociceptive evoked potential as compared to the opposite side of the person's brain, then the computing device may be configured or programmed to generate an alert to communicate to the first responder or rescuer to identify the detected stroke condition. Such an alert can be audible, visual, tactile, or any combination thereof. If there is no difference in response or a difference is not outside of a pre-selected threshold range, then the computing device may be configured so that a stroke event is not detected and no such alert may be provided.

In addition, another form of asymmetry that can be utilized to determine whether a person is or has undergone a stroke is asymmetry between the evoked potential(s) measured from that person based on stimulus provided by the device described herein and a database of "normal" or "control" evoked potentials obtained from individuals who are neurologically intact. The database of "normal" or "control" evoked potentials can be stored on a readable medium associated with a computing system, and processor-implemented programming instructions can compare evoked potentials obtained from the person with one or more evoked potentials from the database, for example, a mean amplitude of "normal" or "control" evoked potentials. In aspects, the database can be continuously updated to provide greater sensitivity.

A computing device can be configured or programmed to collect data from the person and perform various comparisons and/or calculations to determine a neurological state of that person. Those of skill in the art will appreciate that the method can be a known method of determining neurological state, and that those methods will benefit from use of the device disclosed herein. Suitable computing devices, systems, and methods are disclosed in, for example, U.S. Pat. Nos. 8,652,189 and 7,024,238, Chao et al. "Patterns of contact heat evoked potentials (CHEP) in neuropathy with skin denervation: correlation of CHEP amplitude with intra-epidermal nerve fiber density." *Clin Neurophysiol.* 2008; 119(3): 653-661, Chen et al. "Contact heat evoked potentials in normal subjects." *Acta Neurol. Taiwan* 2006; 15: 184-191, Atherton et al. "Use of the novel contact heat evoked potential stimulator (CHEPS) for the assessment of small fibre neurpathy: correlations with skin flare responses and intra-epidermal nerve fibre counts." *BMC Neurology* 2007; 7:21, Hernandez, "Evoked potentials as neurophysiologic tools to evaluate stroke." *J. Neurol. & Stroke* 2015; 2(1): 00046 incorporated herein by reference in their entirety.

Figure 11:
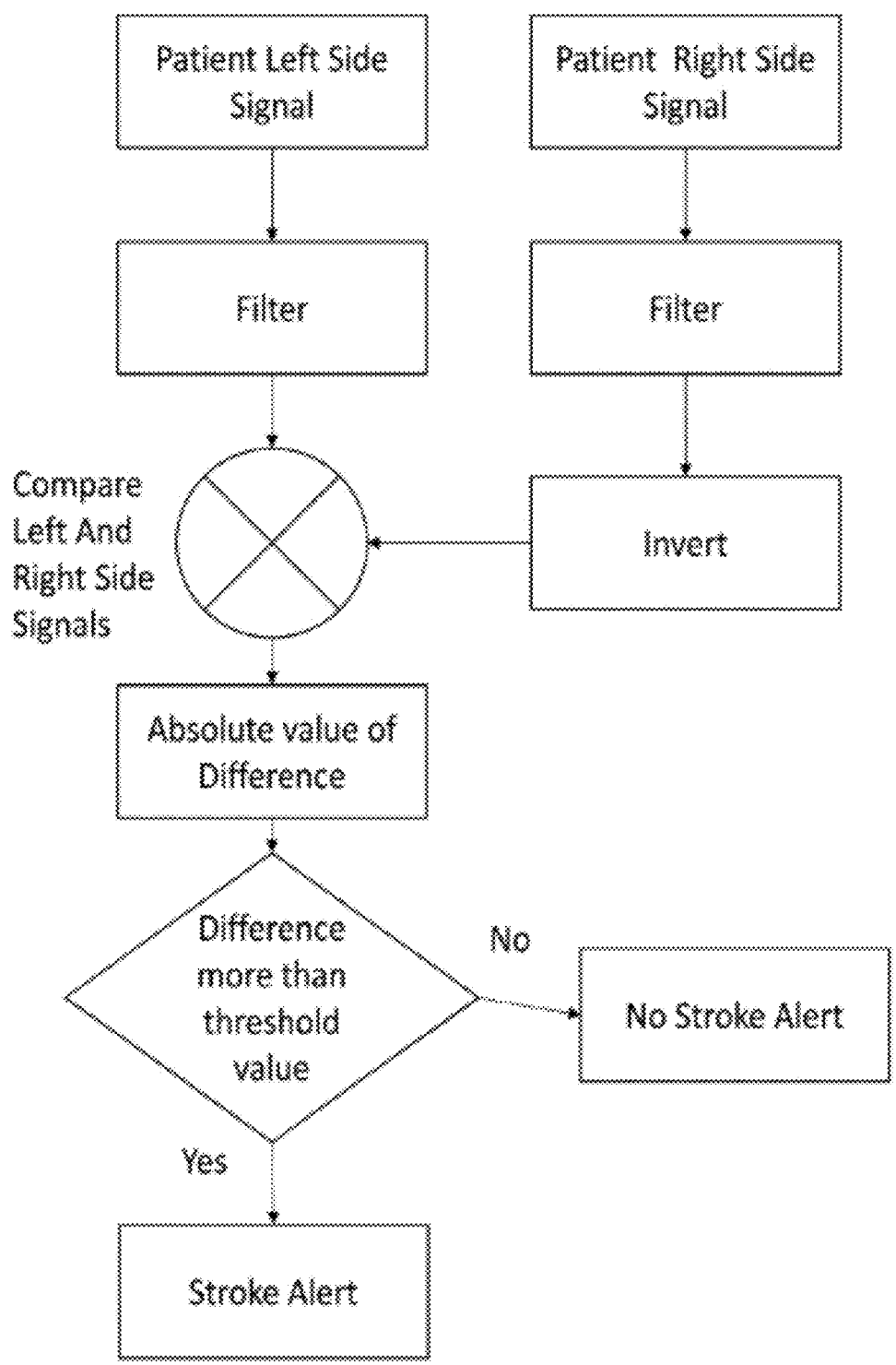
FIG. 11 shows a method of determining whether a stroke has occurred or is occurring, using a device according to one aspect of the present disclosure.
Figure 12:
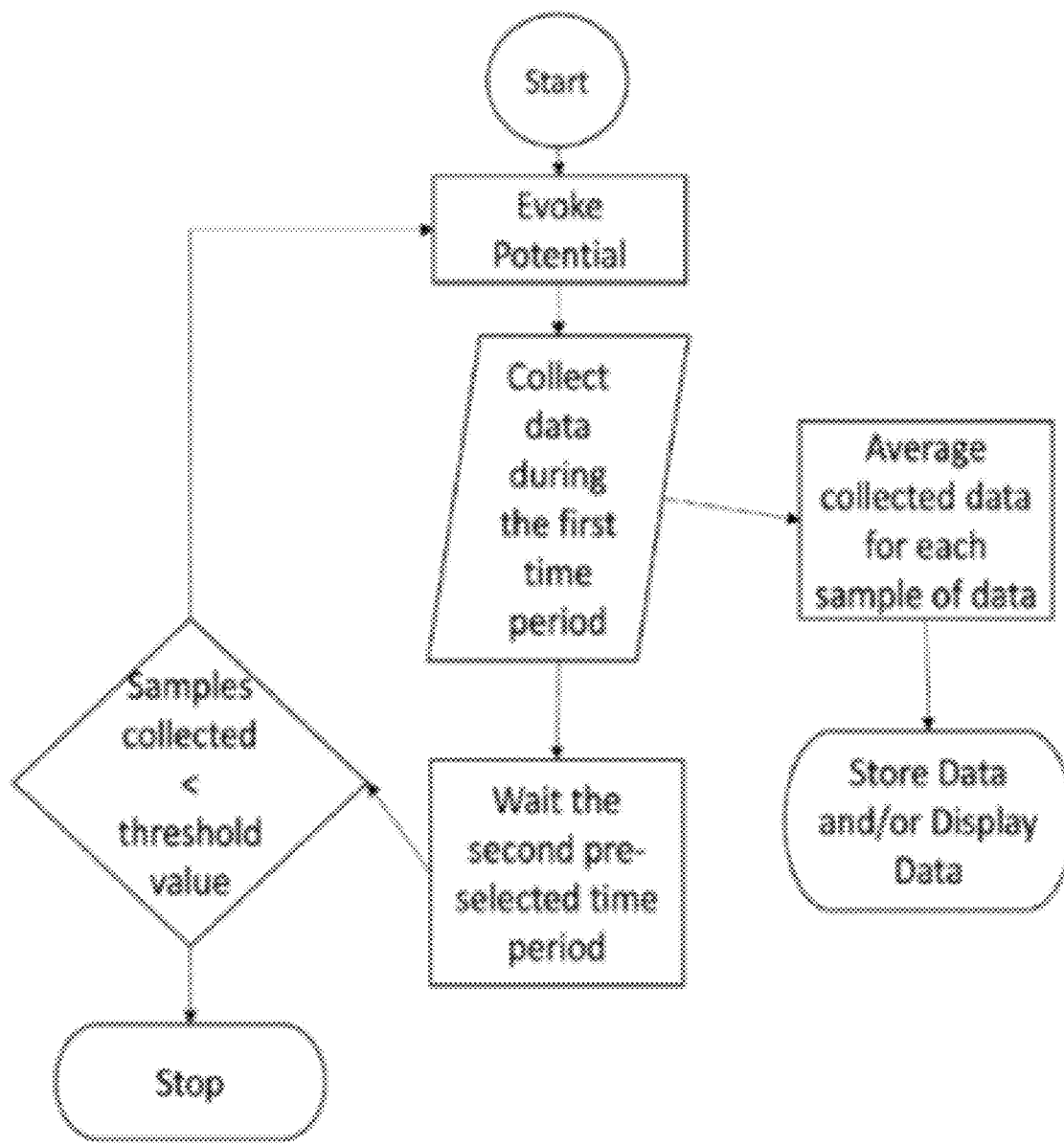
FIG. 12 shows a method of evoking potentials with a device according to one aspect of the present disclosure.

The computing device can be configured or programmed to collect data from the person and perform the comparison of evoked potential data obtained from the person from the right and left sides of the person's body in different ways. FIGS. 11 and 12 illustrate one exemplary comparison method that may be utilized by the computing device. An application stored in the memory of the computing device may define the method to be performed by the computing device by a processor executing the code of the application to perform this comparison.

The code of the application can be stored in one or both of the computing device and/or a central communication server having a processor and non-transitory memory, the server being in communication (wired or otherwise) to the computing device. The code can be updated at the central communication server, and this update may subsequently be communicated to the computing device via a network connection (e.g., an internet connection, a cellular network connection, a local area network connection, a wide area network connection, etc.). The central communication server may also be configured to receive data from different devices to use that data to optimize the code of the application so that the application can provide improved performance after being updated. The updates to the application code made at the central communication server can be periodically transmitted to each of the devices that may be employed in different environments so that the devices may update the code for the applications stored in their memory for updating of their applications and improving the performance of the devices.

Referring to FIG. 11, the computing device may be configured to begin providing thermal stimulation to the person after receiving input to initiate stroke detection and/or monitoring for the person. Such an initiation may occur when the first responder or rescuer selects a button, for example, on a graphical user interface, to provide such input to the computing device. As another example, such initiation of stroke detection and/or stroke monitoring may occur when the computing device detects that the sensors are positioned on a person's head and/or the thermal stimulation device is powered/turned on.

In aspects, thermal stimulation can be delivered so that the left and right sides of the person's body near corresponding left and right side nerves of the person's body each receive the same amount of stimulation for the same amount of time. The sensors can collect data relating to evoked potentials, and that collected data is transmitted to the memory of the computing device and can be saved in a database or data store. The data is collected over at least a first pre-selected time period. This time period may be considered a third pre-selected time period in some embodiments. The third pre-selected time period may only include time within the first pre-selected time period and/or the second pre-selected time period. For instance, the third pre-selected time period may include a portion of the first pre-selected time period or the entirety of the first pre-selected time period in which the person's body is experiencing the evoked potential and may also include additional time that may extend into the second pre-selected time period in which the event potential is not being transmitted into the person's body (e.g., the third pre-selected time period may include time in which the person is being stimulated and may also include time in which the person has ceased being stimulated).

If the number of samples of data collected from the person is not over a pre-selected threshold value, then the computing device may be configured to cause the device to thermally stimulate the skin for the first pre-selected time period again and then cease the providing of that stimulation to the person for the second pre-selected time period so that additional data can be collected by the sensors. The samples of collected data received from the sensors can be stored in the memory of the computing device. In some embodiments, the samples of collected data received by the sensors may be averaged or otherwise manipulated by the processor unit prior to storing that data in a data store in the memory. This process of providing thermal stimulation at separated time intervals by the computing device to collect and store data for assessing the condition of the person may be repeated until the data that is collected from the sensors is over a threshold value for samples of data.

In some embodiments, the computing device can be configured so that between 300-1000 samples per second, all ranges inclusive, of evoked potential data can be collected from the person. In aspects, between 1 and 20, and preferably between 3 and 10, all ranges inclusive, stimulations are performed on a patient, each stimulation period (heating and return to ambient temperature) lasting approximately one second. Thus, for a given patient, between about 900 and 10,000 samples can be collected. Other embodiments may be configured to collect more samples of data per second or less samples of data from the person before making a determination on whether the person may have undergone a stroke or is experiencing a stroke.

The data that is received from each sensor may be stored in a table or other type of database or data store. The data from two or more sensors may each be assigned to a respective column of a table or otherwise grouped so that data from each sensor is grouped separately from data from the other sensors to facilitate the comparison of data from the different sensors. After sufficient data has been collected from the person, the data from a first sensor can be compared to the data collected from a second sensor located on an opposite side of the person's body from the first sensor. An example of how that data can be compared is shown in FIG. 11.

For example, the person's left side signal data can be filtered and the person's right side signal data can also be filtered. The filtration of these data signals may be performed using the same type of filtration methodology. The filtration of the data may be configured to remove noise from the collected data that may be present due to the electrodes or other type of possible interference in the data. An absolute value of a difference between the right and left side signal data is then determined. Such an absolute difference may identify a difference in disregard of whether the difference is a positive or a negative numerical value (e.g., −5 and +5 are treated the same way). If the difference between the right and left side person signal data is below a threshold value, the computing device can be configured to determine that the person has not undergone a stroke or is not undergoing a stroke so that no stroke alert is generated to communicate a warning to the first responder or rescuer. If the difference between the right and left side person signal data is at or over the threshold value, the computing device can be configured to determine that the person has undergone a stroke.

Noise levels can be used by the device to determine a test length for the person. First and second sensors can be positioned on the person prior to providing any thermal stimulation to the person to provide measurement data to the computing device that the device can save and subsequently use to approximate noise levels in the person's current environment. That data can be used by the device to estimate how many samples it will need to correctly diagnose a neurological condition of the person and adapt the number of samples to be taken from the person based on the determined noise level. The number of samples that are needed can be combined with the stimulation rate to communicate to a user via an output device how long the testing of the person (e.g., evaluation of the person to be performed by the device) will take prior to the device beginning to initiate stimulation to the person via the thermal stimulation device described herein.

In some embodiments, noise levels can be measured via sensor data so that the computing device is able to determine a baseline noise environment level prior to performing an evaluation of the person via the thermal stimulation via the device described herein. The sensor can provide measurement data used to determine the electromagnetic noise levels in different environments as well as other noise measurements (e.g., accelerometer related noise concerning motion, etc.). The measurement data obtained prior to the testing of the person can be used by the computing device to perform dynamic environmental filtering so that filters are automatically applied to the measurement data received during testing of a person in which the person's responses to thermal stimulation are collected from the sensors and, subsequently, evaluated by the computing device. In some embodiments, one of multiple different pre-selected measurement data evaluation functions may be utilized by a processor of the computing device to perform the analysis of the received measurement data based on the prior determination of the noise level that was determined to exist prior to the testing being started.

For instance, in some embodiments, the data collected from the sensors can be used to generate a wave form or a curve that identifies a response to an evoked potential of the person based on the data collected from each sensor. Each wave form or curve for corresponding time periods between the first and second sensors can be compared to each other to determine a difference between the amplitude positions of the wave forms at corresponding times (e.g., the difference in amplitude of a signal from the right side of the person's body as compared to the left side of the person's body at the same time at which the data was recorded) or evaluate other morphological features of measurement data of the response of the user to the thermal stimulation that may be provided via the device described herein. If the difference in amplitude positions is greater than or equal to a pre-selected threshold value, then the computing device can be configured to detect the person as having experienced a stroke or undergoing a stroke for generation of a stroke alert for communicating the stroke alert to a first responder/rescuer.

To perform the comparison of the person's left and right side signals, the application can define a pattern recognition methodology used by the processor to evaluate the stored data collected from the sensors, a peak detection methodology used to detect a peak of a waveform of a EEG signal for the data obtained from the sensors, and an amplitude comparator methodology for comparing the absolute differences in amplitude that may exist for that data collected from each sensor. This methodology may incorporate a wave construction technique that is configured to provide wave sorting or spike sorting to differentiate different waves to avoid wave conglomeration to improve the accuracy of the amplitude comparisons being made by the computing device. The application can also be configured so that latency that may exist for data from one sensor as compared to other sensors can be accounted for due to the person's body structure and/or due to the functioning of the electrical communicative components of the stroke detection device.

For instance, in some embodiments the computing device can be configured to perform an evaluation of the measurement data it receives from the sensors. The evaluation of the measurement data can include an evaluation and/or comparison of the subcortical to cortical ratio of the measurement data for the responses of the left and right sides of the body, an evaluation and/or comparison of the absolute amplitudes of the measurement data for the responses of the left and right sides of the body, the first and second derivatives of the measurement data for the responses of the left and right sides of the body, the most significant peak/trough component of the measurement data for the responses of the left and right sides of the body, the absolute latency of the measurement data for the responses of the left and right sides of the body, the amplitude ratio of the measurement data for the responses of the left and right sides of the body, and/or the interpeak latency of the measurement data for the responses of the left and right sides of the body.

It is contemplated that neural networks and/or evolutionary selection algorithms and artificial neural networks can be used to generate binary classification functions and/or other discriminant classification patterns for different races, gender, age, height, and baseline noise environments. Such features can permit the computing device to test a person and account for the demographics of a person and noise environment of a person to improve the reliability and accuracy of the computing device's testing of a person's neurological condition and evaluation of measurement data obtained via that testing. The computing device can also be configured to utilize dynamic averaging of measurement data based on various factors, such as the noise conditions present during a test of a particular person. The computing device can be configured so that the number of discrete stimulations utilized to measure person responses is dynamically determined to provide a sufficient number of samples (e.g., each stimulation and response being a separate sample) to evaluate a person given various applicable conditions that could affect that testing. For example, sufficient data for determining a patient's neurological state can be collected with only 1-20 stimulations (or samples).

In evaluation of measurement data, the measurement data may be evaluated by the computing device to identify various different types of morphological features based on the measurement data received from the sensors. For example, peak amplitude, power, latency, slope, and other morphological features of the measurement data for the person's response(s) to the stimuli for each sample may be identified and assessed. These morphological characteristics of the measurement data may co-vary with each other. Morphological co-variation of the data can be performed by the computing device to estimate locations of sensor placement on the person to identify faulty testing that may provide an unreliable result that should not be used. Upon such a determination being made, a warning may be communicated via an output device to a user so that the person can be retested after the sensor positions and positioning of the device are rechecked to ensure they are correctly positioned on the person.

For instance, in some embodiments, the computing device can be configured so that when a variance of two or more morphological characteristics are far removed from the known co-variance of those characteristics, the conducted test is interpreted as invalid, and a warning is issued to the user via an output device. For example, if an amplitude of a peak is known to vary with slope of another peak by a first factor and a first standard deviation in a given test and the variance between these two factors exceeds a pre-selected co-variance threshold, then the test can be determined to be invalid by the computing device. A third sensor may be positioned for providing a reference signal. The reference signal data can be used to filter out artifacts created by the body and/or environment.

The computing device can also be configured to analyze the sensor data received from the sensors positioned on the person to differentiate between whether a detected condition is due to a hemorrhagic burst and/or an ischemic artery block for one or more identified arteries and, for each artery determined to be blocked, estimate or otherwise determine an extent to which each identified blocked artery is blocked (e.g., fully blocked, 90% blocked, 75% blocked, etc.). For instance, the device can be configured so that amplitudes in measurement data from at least one of the sensors is below a pre-selected threshold, so that a hemorrhage may be detected. In the event major peaks are determined to exist in the amplitudes of the measurement data that are sufficiently below that pre-selected threshold, the device may be configured to detect an ischemic artery block and estimate the degree of blockage based on the amplitude levels of the sensor measurement data. In some embodiments, the measurement of the amount of diffusion due to hemorrhagic stroke by use of a far field effects can be used. An abnormal attenuation of signal between two or more points on the brain from such measurement can be indicative of a hemorrhagic stroke, and the computing device can be configured to identify such an occurrence via sensors providing measurement data, providing data that indicates such an occurrence exists. This information can also be communicated to a hospital server, or any computing device at a hospital, to help facilitate the providing of care to the person when the person is transported to the hospital.

Embodiments of the computing device can also be configured to utilize machine learning techniques to continually update and optimize how the measurement data is evaluated for subsegments of a population of persons that may have undergone a stroke or other neurological conditions. The computing device may start with a sample of a pre-selected number of persons (e.g., 100, 200, 300, etc.) and optimize its measurement data evaluation methodology based on testing results that it saves in its memory as more persons are evaluated by the computing device. The evaluation optimization process can be based on the stored data from prior tests to provide changes to different pre-selected variables that are used to assess different persons having different demographics. In some embodiments, multiple computing devices employed in different care environments may communicate the measurement data and evaluation data from prior testing of persons to a central server via at least one communication connection. The central server may evaluate that data and update various variables used by the applications of those computing devices for evaluating measurement data. The updated application variables may then be communicated to the communication devices so that the application of the devices can be updated so that subsequent testing of persons performed by the computing devices utilized the updated evaluation methodology and updated variable information communicated by the central server.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A portable thermal stimulation device for delivering thermal stimulation to a person for the purpose of producing evoked potentials, comprising:
   a housing having an opening;
   an air circulator configured to provide a current of air through the opening in the housing to a person's skin;
   a heating element configured to heat the current of air provided by the air circulator; and
   an attachment mechanism to secure the device to the person with the opening of the housing positioned against the person's skin,
   wherein the air circulator directs the current of air across the heating element to generate heated air which is then directed out of the opening in the housing to the person's skin, and
   wherein the heated air produces heat-evoked potentials in the person.

2. The portable thermal stimulation device according to claim 1, further comprising an insulating layer disposed at least partially within or on the housing.

3. The portable thermal stimulation device according to claim 1, wherein the air circulator is positioned at least partially within the housing.

4. The portable thermal stimulation device according to claim 1, wherein the air circulator is at least one of a pump, a compressor, a fan, a blower, an impeller, and a source of pressurized air.

5. The portable thermal stimulation device according to claim 1, wherein the device further comprises one or more rechargeable batteries.

6. The portable thermal stimulation device according to claim 1, wherein the heating element is positioned at least partially within the housing.

7. The portable thermal stimulation device according to claim 1, wherein the heating element is at least one of an electrical heating element and a chemical heating element.

8. The portable thermal stimulation device according to claim 7, wherein the electrical heating element comprises a resistive element.

9. The portable thermal stimulation device according to claim 1, further comprising at least one temperature sensor disposed within the housing, and wherein the at least one temperature sensor is configured to measure the temperature of the current of air within the housing and/or temperature of a portion of skin of the person to which the device is attached.

10. The portable thermal stimulation device according to claim 9, further comprising:
    a processor; and
    a non-transitory computer readable media storing programming instructions that, when executed by the processor cause the processor to analyze temperature data received from the one or more temperature sensors, compare the temperature data to a predetermined threshold, and adjust a temperature of the current of air based on the comparison.

11. The portable thermal stimulation device according to claim 1, further comprising one or more air-directing mechanisms configured to direct the current of air to one or more areas of the person's skin.

12. The portable thermal stimulation device according to claim 1, further comprising at least one source of air in fluid communication with the air circulator.

13. The portable thermal stimulation device according to claim 12, wherein the at least one source of air comprises a cartridge attached to the housing.

14. The portable thermal stimulation device according to claim 12, wherein at least one source of air is a source of cool air and wherein at least one source of air is a source of warm air.

15. The portable thermal stimulation device according to claim 14, further comprising a manifold or mixer in fluid communication with the at least two sources of air and the housing.

16. The portable thermal stimulation device according to claim 1, further comprising a cooling element adapted to cool the current of air provided by the air circulator.

17. A system for determining a neurological state of a person, comprising:
    the thermal stimulation device of claim 1;
    one or more sensors configured to be attached to the person;
    a processor; and
    a non-transitory computer readable media storing programming instructions that, when executed, cause the processor to analyze data received from the one or more sensors and determine the person's neurological state.

18. The system according to claim 17, wherein the non-transitory computer readable media stores programming instructions that, when executed, cause the thermal stimulation device to thermally stimulate a portion of the person's skin.

19. A method of determining a neurological condition in a person, comprising:
- thermally stimulating a portion of the person's skin with the thermal stimulation device of claim 1;
- detecting, with one or more sensors attached to the person, an evoked potential in the person's primary somatosensory cortex, somatosensory association cortex, and/or thalamus;
- receiving, with one or more processors and from the sensors, data relating to the evoked potentials; and
- analyzing, with one or more processors, the evoked potentials to determine a neurological condition of the person.

20. The method according to claim 19, wherein the person's skin is thermally stimulated 1-20 times for 100-500 ms.

\* \* \* \* \*